United States Patent [19]

Nickisch et al.

[11] Patent Number: 4,559,331
[45] Date of Patent: Dec. 17, 1985

[54] 7α-SUBSTITUTED 3-OXO-17α-PREGN-4-ENE-21,17-CARBOLACTONES, PROCESS FOR THEIR PRODUCTION, AND PHARMACEUTICAL PREPARATIONS CONTAINING SAME

[75] Inventors: Klaus Nickisch; Henry Laurent; Peter Esperling; Dieter Bittler; Rudolf Wiechert; Wolfgang Losert, all of Berlin, Fed. Rep. of Germany

[73] Assignee: Schering Aktiengesellschaft, Berlin and Bergkamen, Fed. Rep. of Germany

[21] Appl. No.: 641,599

[22] Filed: Aug. 17, 1984

[30] Foreign Application Priority Data

Aug. 17, 1983 [DE] Fed. Rep. of Germany ....... 3330086
Aug. 17, 1983 [DE] Fed. Rep. of Germany ....... 3330084
Aug. 17, 1983 [DE] Fed. Rep. of Germany ....... 3330085

[51] Int. Cl.⁴ ............................................ A61K 31/58
[52] U.S. Cl. ................................. 514/173; 260/239.57
[58] Field of Search ................... 260/239.57; 424/241; 514/173

[56] References Cited

U.S. PATENT DOCUMENTS

| 4,129,564 | 12/1978 | Wiechert et al. | 260/239.57 |
| 4,291,029 | 9/1981 | Wiechert et al. | 260/239.57 |
| 4,450,107 | 5/1984 | Nickisch et al. | 260/239.57 |
| 4,450,170 | 5/1984 | Beeley et al. | 424/273 R |
| 4,500,522 | 2/1985 | Nickisch et al. | 260/239.57 |

Primary Examiner—Elbert L. Roberts
Attorney, Agent, or Firm—Millen & White

[57] ABSTRACT

Novel 7α-substituted 3-oxo-17α-pregn-4-ene-21,17-carbolactones of the formula

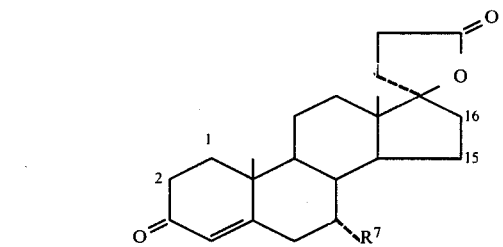

wherein

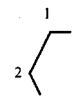

is a CC single or CC double bond or the group

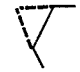

$R^7$ is the group SR', R' being a hydrogen atom or a straight-chain or branched alkyl residue of 1-6 carbon atoms optionally substituted by a hydroxy or acyloxy group, the group COOR" or the group COR" wherein R" is an alkyl group of 1-4 carbon atoms and

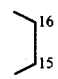

is a CC single bond or the group

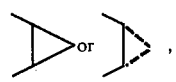

have antialdosterone activity with reduced endocrinological side effects.

32 Claims, No Drawings

7α-SUBSTITUTED 3-OXO-17α-PREGN-4-ENE-21,17-CARBOLACTONES, PROCESS FOR THEIR PRODUCTION, AND PHARMACEUTICAL PREPARATIONS CONTAINING SAME

The present invention relates to novel 7α-substituted 3-oxo-17α-pregn-4-ene-21,17-carbolactones, a process for their preparation, and pharmaceutical preparations containing them.

SUMMARY OF THE INVENTION

It is an object of this invention to provide new compounds having valuable pharmacological properties.

Upon further study of the specification and appended claims, further objects and advantages of this invention will become apparent to those skilled in the art.

These objects have been attained by providing 7α-substituted 3-oxo-17α-pregn-4-ene-21,17-carbolactones of Formula I

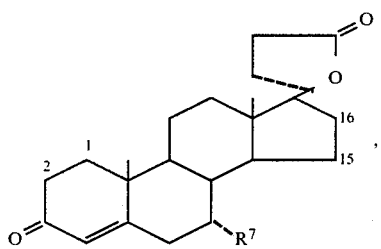

wherein

is a CC single or CC double bond or the group

R⁷ is the group SR' wherein R' is hydrogen or a straight-chain or branched alkyl group of 1–6 carbon atoms, optionally substituted by a hydroxy or acyloxy group; the group COOR''; or the group COR'', wherein
R'' is an alkyl group of 1–4 carbon atoms and

is a CC single bond or the group

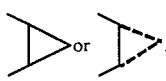

DETAILED DISCUSSION

R' in Formula I can be a straight-chain or branched alkyl residue of 1–6 carbon atoms optionally substituted by a hydroxy or acyloxy group. Examples include, for example, methyl, ethyl, propyl, isopropyl, hydroxy- or acetoxyethyl, 1- or 2-hydroxy- or acetoxypropyl, or a butyl, pentyl or hexyl group, etc. The alkyl groups, when substituted, are generally substituted by 1–3 OH or acyloxy groups. Preferred acyloxy groups are $C_{1-4}$-alkanoyloxy groups. R'' alkyl groups are those mentioned above which are of 1–4 C-atoms.

The novel compounds of Formula I have the properties of neutralizing or reversing the effect of aldosterone or deoxycorticosterone on the elimination of sodium and potassium salts. The compounds of this invention are thus useful for the treatment of certain forms of hypertension, i.e., hypertension mainly as the result of primary or secondary hyperaldosteronism; of edemas, for example in the case of cardiac insufficiency, or cirrhosis of the liver, or nephrotic syndrome; of primary and secondary aldosteronism; and of other endocrine disturbances caused by aldosterone. They can furthermore be used as diuretics.

The novel active agents have the advantage over the commercially available spironolactone and its metabolites containing a mercapto or methylthio group in the 7α-position instead of the acetylthio group (Steroids 20:41 [1972]), of higher activity and longer duration of efficacy. They furthermore show reduced antiandrogenic and progestational side effects.

The compounds of this invention containing at least one 1α,2α- or 15α,16α-methylene group surprisingly prove to be especially superior in their antialdosterone effect to the known spironolactone in a test model according to Hollmann (Naunyn-Schmiedebergs Arch. Exp. Path. Pharmak. 247:419 [1964]). They are also distinguished by lower antiandrogenic side effects over spironolactone and the corresponding compounds of German Laid-Open Application No. 3,111,951 which lack a 1α,2α- or 15α,16α-methylene group.

The antiandrogenic effect is found in compounds which themselves do not possess androgenic activity but which, due to their high binding affinity, displace the body's own androgen entirely or partially from the receptor, as is observed to a certain extent in the case of spironolactone. It has been found that the novel compounds of Formula I show a lower affinity to the androgen receptor than spironolactone.

The compounds of this invention wherein R⁷ is COR'' show, in the test model by Hollmann (Naunyn-Schmiedebergs Arch. Exp. Path. Pharmak. 247:419 [1964]), an antialdosterone activity comparable to that of spironolactone. In contrast to spironolactone, however, the compounds of this invention do not bind to the androgen and gestagen receptor. This means that the novel compounds are free of antiandrogenic and progestational side effects.

Consequently, the novel compounds of Formula I are suitable for the treatment of edemas, for example in the case of grave cardiac insufficiency, or in the case of cirrhosis of the liver or nephrotic syndrome, as well as pathological conditions involving primary or secondary hyperaldosteronism.

The following compounds prove to be especially valuable from a pharmacological viewpoint:
1. 7α-Mercapto-1α,2α-methylene-3-oxo-17α-pregn-4-ene-21,17-carbolactone.
2. 7α-Methylthio-1α,2α-methylene-3-oxo-17α-pregn-4-ene-21,17-carbolactone.

3. 7α-Ethylthio-1α,2α-methylene-3-oxo-17α-pregn-4-ene-21,17-carbolactone.
4. 7α-Propylthio-1α,2α-methylene-3-oxo-17α-pregn-4-ene-21,17-carbolactone.
5. 7α-(2-Propylthio)-1α,2α-methylene-3-oxo-17α-pregn-4-ene-21,17-carbolactone.
6. 7α-Butylthio-1α,2α-methylene-3-oxo-17α-pregn-4-ene-21,17-carbolactone.
7. 7α-(2-Hydroxyethylthio)-1α,2α-methylene-3-oxo-17α-pregn-4-ene-21,17-carbolactone.
8. 7α-Mercapto-3-oxo-17α-pregna-1,4-diene-21,17-carbolactone.
9. 7α-Methylthio-3-oxo-17α-pregna-1,4-diene-21,17-carbolactone.
10. 7α-Mercapto-15β,16β-methylene-3-oxo-17α-pregn-4-ene-21,17-carbolactone.
11. 7α-Mercapto-15β,16β-methylene-3-oxo-17α-pregna-1,4-diene-21,17-carbolactone.
12. 7α-Mercapto-1α,2α;15β,16β-dimethylene-3-oxo-17α-pregn-4-ene-21,17-carbolactone.
13. 7α-Methylthio-15β,16β-methylene-3-oxo-17α-pregn-4-ene-21,17-carbolactone.
14. 7α-Ethylthio-15β,16β-methylene-3-oxo-17α-pregn-4-ene-21,17-carbolactone.
15. 7α-Propylthio-15β,16β-methylene-3-oxo-17α-pregn-4-ene-21,17-carbolactone.
16. 7α-Butylthio-15β,16β-methylene-3-oxo-17α-pregn-4-ene-21,17-carbolactone.
17. 7α-Methylthio-15β,16β-methylene-3-oxo-17α-pregna-1,4-diene-21,17-carbolactone.
18. 7α-(2-Hydroxyethylthio)-15β,16β-methylene-3-oxo-17α-pregn-4-ene-21,17-carbolactone.
19. 7α-(2-Hydroxyethylthio)-15β,16β-methylene-3-oxo-17α-pregna-1,4-diene-21,17-carbolactone.
20. 7α-(2-Acetoxyethylthio)-15β,16β-methylene-3-oxo-17α-pregn-4-ene-21,17-carbolactone.
21. 7α-(2-Hydroxypropylthio)-15β,16β-methylene-3-oxo-17α-pregn-4-ene-21,17-carbolactone.
22. 7α-Mercapto-15α,16α-methylene-3-oxo-17α-pregn-4-ene-21,17-carbolactone.
23. 7α-(2-Hydroxyethylthio)-15α,16α-methylene-3-oxo-17α-pregn-4-ene-21,17-carbolactone.
24. 7α-(2-Hydroxyethylthio)-1α,2α;15β,16β-dimethylene-3-oxo-17α-pregn-4-ene-21,17-carbolactone.
25. 7α-(2-Hydroxypropylthio)-1α,2α;15β,16β-dimethylene-3-oxo-17α-pregn-4-ene-21,17-carbolactone.
26. 7α-Mercapto-1α,2α;15α,16α-dimethylene-3-oxo-17α-pregn-4-ene-21,17-carbolactone.
27. 7α-Methylthio-1α,2α;15α,16α-dimethylene-3-oxo-17α-pregn-4-ene-21,17-carbolactone.
28. 7α-Methylthio-15α,16α-methylene-3-oxo-17α-pregn-4-ene-21,17-carbolactone.
29. 7α-(2-Hydroxyethylthio)-1α,2α;15α,16α-dimethylene-3-oxo-17α-pregn-4-ene-21,17-carbolactone.
30. 7α-Methylthio-1α,2α;15β,16β-dimethylene-3-oxo-17α-pregn-4-ene-21,17-carbolactone.
31. 7α-Ethylthio-1α,2α;15β,16β-dimethylene-3-oxo-17α-pregn-4-ene-21,17-carbolactone.
32. 7α-(3-Hydroxypropylthio)-1α,2α;15β,16β-dimethylene-3-oxo-17α-pregn-4-ene-21,17-carbolactone.
33. 7α-Methoxycarbonyl-15α,16α-methylene-3-oxo-17α-pregn-4-ene-21,17-carbolactone.
34. 7α-methoxycarbonyl-1α,2α-methylene-3-oxo-17α-pregn-4-ene-21,17-carbolactone.
35. 7α-Ethoxycarbonyl-1α,2α-methylene-3-oxo-17α-pregn-4-ene-21,17-carbolactone.
36. 7α-Isopropoxycarbonyl-1α,2α-methylene-3-oxo-17α-pregn-4-ene-21,17-carbolactone.
37. 7α-Methoxycarbonyl-1α,2α;15β,16β-dimethylene-3-oxo-17α-pregn-4-ene-21,17-carbolactone.
38. 7α-Ethoxycarbonyl-1α,2α;15β,16β-dimethylene-3-oxo-17α-pregn-4-ene-21,17-carbolactone.
39. 7α-Propoxycarbonyl-1α,2α;15β,16β-dimethylene-3-oxo-17α-pregn-4-ene-21,17-carbolactone.
40. 7α-Isopropoxycarbonyl-1α,2α;15β,16β-dimethylene-3-oxo-17α-pregn-4-ene-21,17-carbolactone.
41. 7α-Methoxycarbonyl-1α,2α;15α,16α-dimethylene-3-oxo-17α-pregn-4-ene-21,17-carbolactone.
42. 7α-Methoxycarbonyl-15α,16α-methylene-3-oxo-17α-pregna-1,4-diene-21,17-carbolactone.
43. 7α-Acetyl-15β,16β-methylene-3-oxo-17α-pregn-4-ene-21,17-carbolactone.
44. 7α-(1-Oxopropyl)-15β,16β-methylene-3-oxo-17α-pregn-4-ene-21,17-carbolactone.
45. 15β,16β-Methylene-3-oxo-7α-(1-oxobutyl)-17α-pregn-4-ene-21,17-carbolactone.
46. 7α-Acetyl-1α,2α-methylene-3-oxo-17α-pregn-4-ene-21,17-carbolactone.
47. 7α-Acetyl-1α,2α;15β,16β-dimethylene-3-oxo-17α-pregn-4-ene-21,17-carbolactone.
48. 7α-(1-Oxopentyl)-1α,2α;15β,16β-dimethylene-3-oxo-17α-pregn-4-ene-21,17-carbolactone.

The following table demonstrates the antialdosterone activity on rats, as well as the magnitude of the competition factors (CF) as a measure of the binding to the androgen and to the gestagen receptors, respectively.

In this connection, the symbols mean:

(+)—Significantly poorer efficacy of the test compound.

(++)—Significantly identical efficacy of the test compound (with 8 mg/animal) as compared with the standard compound.

(+++)—Significantly better efficacy of the test compound (with 8 mg/animal) as compared with the standard compound.

∞—Off scale. At least greater than 500.

The higher the CF value, the lower the respective antiandrogenic or antigestagenic effect.

TABLE

| Compound No. or Designation | Antialdosterone Effect on Rats | Binding to Androgen Receptor [CF] | Binding to Gestagen Receptor [CF] |
|---|---|---|---|
| Spironolactone (SPL) | 1 | 8.9 | 21 |
| 1 | +++ | 4.4 | 33 |
|  | 1.4 × SPL |  |  |
| 3 | +++ | 9.2 | 36 |
| 12 | +++ | 8.2 | 29 |
| 13 | 0.95 × SPL | 87 | 75 |
| 17 | ~ SPL | 82 | 47 |
| 18 | ++ | ∞ | ∞ |
|  | 0.6 × SPL |  |  |
| 21 | 1.2 × SPL | ∞ | ∞ |
| 27 | +++ | 15 | 42 |
| 30 | 1.5 × SPL | 21 | ∞ |
| 31 | 1.5 × SPL | 13 | 32 |
| 33 | 1.4 × SPL | 121 | 10 |
| 35 | ++ | 30 | 35 |
| 37 | 1.3 × SPL | 29 | 92 |
| 38 | 1.8 × SPL | 28 | 34 |
| 40 | 1.4 × SPL | 40 | 19 |
| 41 | 1.4 × SPL | 53 | 98 |
| 43 | 0.8 × SPL | 301 | ∞ |
| 47 | ++ | 131 | ∞ |

The administration of the novel active agents of this invention is analogous to that of the known agent spironolactone. The dose of active agent lies below that of spironolactone. Moreover, based in part on their longer-lasting effectiveness, the novel active agents need normally be administered only once a day. Typical doses are 10–100 mg/day for the diuretic use; 10–200 mg/day for the antialdosterone uses in general; 5–50 mg/day for the treatment of hypertension; and 10–50 mg/day for the treatment of edemas.

The active agents can be processed according to conventional methods of galenic pharmacy to prepare pharmaceutical preparations, preferably for enteral administration. Especially suitable for enteral administration are tablets, dragees, or capsules containing, per dosage unit, about 5–200 mg of active ingredient in an inert excipient.

The pharmacologically active compounds of this invention can be processed in accordance with conventional methods of galenic pharmacy to produce for administration to patients, e.g., mammals including humans. Conventional excipients are pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, gum arabic, polyethylene glycols, gelatine lactose, amylose, magnesium stearate, talc, silicic acid, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Dosages for a given host can be determined using conventioanl considerations, e.g., by customary comparison of the differential activities of the subject compound and of a known agent by means of an appropriate, conventional pharmacological protocol.

The compounds of this invention of Formula I can be produced in accordance with conventional methods, e.g., by the following general methods:
when $R^7$ is SH,
saponifying a corresponding 7α-thioester of Formula II

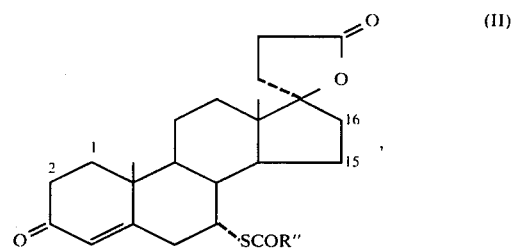

wherein R'',

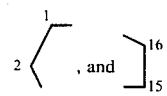

are as defined for Formula I;
when $R^7$ is the group SR' wherein R' is a straight-chained or branched alkyl residue, optionally substituted by hydroxy,
adding a thioalcohol of the formula

R''—SH wherein R'' is as defined for Formula I, to a $\Delta^6$-unsaturated compound of Formula III

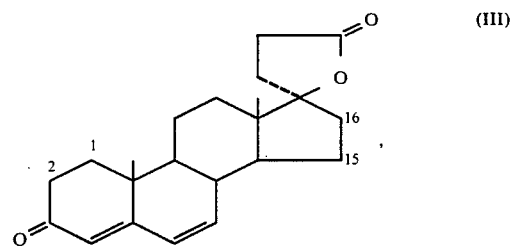

wherein

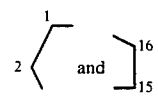

are as defined for Formula I;
when $R^7$ is the group COOR'',
reacting a 7α-carboxy compound of Formula IV

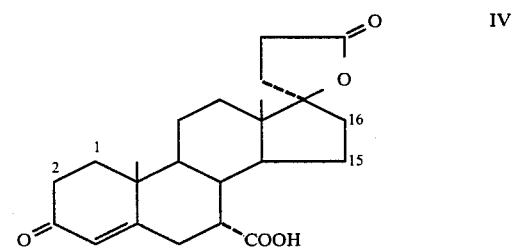

wherein

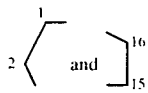

are as defined for Formula I, to form the corresponding $C_1$–$C_4$-alkyl ester;

when $R^7$ is the group COR'', reacting 7α-formyl compound of Formula V

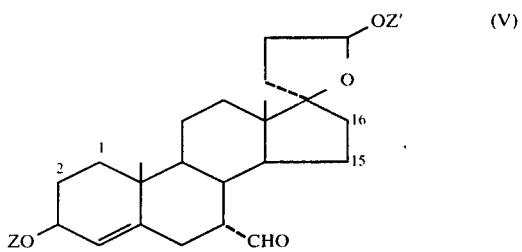

wherein

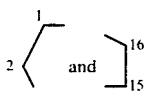

are as defined for Formula I and Z and Z' each are a blocking silyl group, with an organometallic compound R''—X, wherein R'' is as defined for Formula I and X is lithium or a magnesium halide, and treating the resultant 7α-(1-hydroxyalkyl) compound of Formula VI

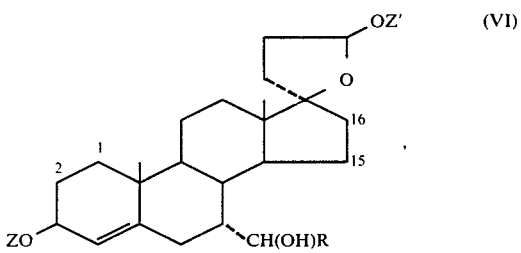

wherein R is the alkyl group R'', with an acidic oxidizing agent for silyl ether cleavage and oxidation of the hydroxy groups; and optionally, introducing the $\Delta^1$-double bond and/or optionally, esterifying a free hydroxy group to form the $R^7$; SR' group containing an acyloxy substituent.

In order to produce the 7α-mercapto compounds (R'=H), the corresponding 7α-thioesters of Formula II (R''=a lower alkyl residue) are conventionally saponified. For example, the saponification can be carried out with bases in an alcoholic solution, such as potassium or sodium methylate or ethylate, in methanol or ethanol. The preferred lower alkyl residue R'' is the methyl or ethyl residue.

In order to prepare the 7α-alkylthio compounds (R''=a straight-chain or branched alkyl residue of 1–6 carbon atoms, optionally substituted by a hydroxy group), a thioalcohol of the formula R''—SH, wherein R'' has the meanings given above, is added to the $\Delta^6$-unsaturated compound of Formula III. The reaction can be conducted in an alkaline medium in the presence of a protonic solvent, such as methanol or ethanol at temperatures of 0°–30° C. Especially suitable bases are secondary or tertiary amines, such as diethylamine and piperidine.

The 7α-carboxy compounds of Formula IV are esterified according to methods known per se. Thus, it is possible, for example, to react the 7α-carboxylic acid with a diazoalkane, e.g., diazomethane or diazoethane, in a suitable solvent, such as diethyl ether, tetrahydrofuran, or dioxane, or in a mixture of these solvents, at a temperature of 0°–30° C., and to then decompose excess diazoalkane by adding an organic acid, such as acetic or tartaric acid, and to free the solution of solvent under vacuum.

However, the esterification can also be performed by reacting the carboxylic acid of Formula IV according to known methods with chloroformic acid alkyl ester in a suitable solvent, such as tetrahydrofuran or dioxane, in the presence of a tertiary amine, e.g., triethylamine, at a temperature of 0°–30° C. to obtain the mixed anhydride (COOCO-alkyl), and heating the latter to boiling with the alcohol R''OH (wherein R'' has the meanings given for Formula I).

According to another version, the carboxylic acid can be directly converted to the corresponding ester with the alcohol, R''OH in the presence of a condensation agent, e.g., dicyclohexylcarbodiimide. Also the reaction of the carboxylic acid with haloalkanes, for example bromoethane or iodopropane, in the presence of silver oxide, leads to the desired esters of Formula I.

In order to produce compounds of Formula I wherein $R^7$ is an oxoalkyl group, the corresponding formyl compound of Formula V wherein the free hydroxy groups are silylated, can be reacted with an organometallic compound R''—X wherein R'' has the meanings given for Formula I and X is lithium or a magnesium halide. The thus-obtained 7α-(1-hydroxyalkyl) compound of Formula VI can be treated, for silyl ether cleavage and oxidation of the hydroxy groups, with an acidic oxidizing agent.

Suitable silyl residues Z and Z' include trialkylsilyl residues, especially trimethyl- or dimethyl-tertbutylsilyl residues, or triaryl- or triarylalkylsilyl residues, e.g., triphenyl- and tribenzylsilyl residues, furthermore also dialkylsilyl, e.g., dimethylsilyl residues.

Reaction with the organometallic compond R''—X takes place conventionally. Suitable organometallic compounds are, in particular, alkyllithium, such as methyl-, ethyl-, propyl-, and butyllithium. The organometallic compound, however, can also be a Grignard compound, for example, methyl-, ethyl-, propyl-, or butylmagnesium bromide or -magnesium iodide. The reaction can be conducted in solvents, such as dialkyl ethers, tetrahydrofuran, dioxane, benzene, or toluene, at temperatures from room temperature to the boiling point of the respective solvent.

Silyl ether cleavage and oxidation of the hydroxy groups can be conducted with an acidic oxidizing agent. A preferred oxidizing agent is chromium trioxide in sulfuric acid, for example Jones solution.

The optional subsequent introduction of the $\Delta^1$-double bond can take place conventionally by chemical or microbiological methods. Suitable chemical dehydrogenation agents for the 1,2-dehydrogenation include, for example, selenium dioxide, 2,3-dichloro-5,6-dicyanobenzoquinone, chloranil, tallium triacetate, or lead tetraacetate. Suitable microorganisms for the 1,2-dehydrogenation include, for example, schizomycetes, especially those of the genera Arthrobacter, e.g., *A. simplex* (ATCC 6946); Bacillus, e.g., *B. lentus* (ATCC 13805), or *B. sphaericus* (ATCC 7055); Pseudomonas, e.g., *P. aeruginosa* (IFO 3505); Flavobacterium, e.g., *F. flavescens* (IFO 3058), etc. The 1,2-dehydrogenation is preferably performed by chemical methods. For this purpose, the 1,2-dihydro steroid can be heated in a suitable solvent with the dehydrogenating agent over a relatively long period of time to 60°–120° C. Suitable solvents include, for example, dioxane, toluene, benzene, tetrahydrofuran, tert-butanol, and mixtures of these solvents. The reaction is completed after several hours. It is recommended to observe the reaction by thin-layer chromatography. The reaction mixture is worked up after the starting material has been converted.

The optionally following esterification of a hydroxy group contained in substituent R' is conducted according to the processes customary in steroid chemistry. Esterification takes place preferably with a derivative of a lower aliphatic carboxylic acid in the presence of pyridine and/or 4-dimethylaminopyridine. Especially suitable derivatives are anhydrides and halogenides of lower carboxylic acids, particularly acetic, propionic, butyric, and valeric acid.

The starting compounds required for performing the process of this invention are either known (for example, from U.S. Pat. No. 4,129,564) or can be prepared according to one of the methods described below or others, always from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

Preparation of the Starting Compounds

A.

1α,2α-Methylene-3-oxo-17α-pregna-4,6-diene-21,17-carbolactone

A solution of 15.7 g of trimethylsulfoxonium iodide in 150 ml of dimethyl sulfoxide is combined under argon with 2.84 g of a 55% suspension of sodium hydride in mineral oil and stirred until a clear solution is produced. Then 10 g of 3-oxo-17α-pregna-1,4,6-triene-21,17-carbolactone is added in solid form. The mixture is worked up after about 45 minutes by pouring into ice water weakly acidified with hydrochloric acid. The thus-precipitated product is removed by filtration, washed with water, dried, and thereafter chromatographed on silica gel. After recrystallization from acetone-hexane, 8.73 g of 1α,2α-methylene-3-oxo-17α-pregna-4,6-diene-21,17-carbolactone is obtained, mp 253.7° C. $[\alpha]_D = +176°$ (in chloroform). UV: $\epsilon_{282} = 21,100$ (in methanol).

B.

7α-Acethylthio-1α,2α-methylene-3oxo-17α-pregn-4-ene-21,17-carbolactone

A solution of 5.1 g of 1α,2α-methylene-3-oxo-17α-pregna-4,6-diene-21,17-carbolactone in 100 ml of methanol is combined with 20.5 ml of water and 10 ml of thioacetic acid and allowed to stand for 5 hours at room temperature. The mixture is diluted with diethyl ether, washed with sodium bicarbonate solution and water, dried over sodium sulfate, and evaporated under vacuum. The residue is chromatographed on silica gel, thus obtaining 3.28 g which yields, when recrystallized from dichloromethane-diisopropyl ether, 2.04 g of 7α-acetylthio-1α,2α-methylene-3-oxo-17α-pregn-4-ene-21,17-carbolactone, mp 224.3° C. $[\alpha]_D = +90°$ (in chloroform). UV: $\epsilon_{235} = 16,000$ (in methanol).

C.

7α-Acetylthio-15β,16β-methylene-3-oxo-17α-pregna-1,4-diene-21,17-carbolactone 1.5 g of 7α-acetylthio-15β,16β-methylene-3-oxo-17α-pregn-4-ene-21,17-carbolactone is refluxed with 50 ml of benzene and 1.5 g of 2,3-dichloro-5,6-dicyano-1,4-benzoquinone for 24 hours. The reaction solution is diluted with diethyl ether, washed with sodium bicarbonate solution and water, dried, and evaporated. The residue is purified by column chromatography on silica gel, thus obtaining 820 mg of 7α-acetylthio-15β,16β-methylene-3-oxo-17α-pregna-1,4-diene-21,17-carbolactone, mp 280.6° C. $[\alpha]_D = -86°$ (in chloroform).

D.

7α-Acetylthio-1α,2α;15α,16α-dimethylene-3-oxo-17α-pregn-4-ene-21,17-carbolactone 1. 5.0 g of 15α,16α-methylene-3-oxo-17α-pregna-4,6-diene-21,17 carbolactone is stirred in 50 ml of dioxane with 5.0 g of 2,3-dichloro-5,6-dicyano-1,4-benzoquinone for 3 hours at 100° C. The reaction solution is then cooled, the thus-precipitated hydroquinone is suctioned off and washed with dioxane. The filtrate is extensively concentrated under vacuum. The residue is taken up in diethyl ether, washed with sodium bicarbonate solution and water, dried, and evaporated. After chromatography on silica gel, 3.46 g of 15α,16α-methylene-3-oxo-17α-pregna-1,4,6-triene-21,17-carbolactone is obtained. UV: $\epsilon_{222} = 11,250$, $\epsilon_{254} = 9,140$, $\epsilon_{299} = 11,500$ (in methanol).

2. 8.8 g of trimethylsulfoxonium iodide is stirred in 99 ml of dimethyl sulfoxide with 1.39 g of sodium hydride, a 55% oil suspension, until the hydride has been dissolved. Then, under argon, 2.8 g of 15α,16α-methylene-3-oxo-17α-pregna-1,4,6-triene-21,17-carbolactone is added thereto, and the mixture is agitated for 2 hours at room temperature. The reaction solution is stirred into ice water, weakly acidified with 2N sulfuric acid, and the thus-formed precipitate is filtered off. After dissolving in methylene chloride, the reaction mixture is washed with water, dried, and evaporated. The residue is chromatographed on silica gel, thus producing 2.1 g of 1α,2α;15α,16α-dimethylene-3-oxo-17α-pregna-4,6-diene-21,17-carbolactone. UV: $\epsilon_{281} = 19,500$ (in methanol).

3. 1.0 g of 1α,2α;15α,16α-dimethylene-3-oxo-17α-pregna-4,6-diene-21,17-carbolactone is stirred in 20 ml of methanol with 4 ml of water and 1.5 ml of thioacetic acid for 16 hours at room temperature. The reaction solution is then diluted with diethyl ether, washed with sodium bicarbonate solution and water, dried, and evaporated. The residue is chromatographed on silica gel. Recrystallization from diisopropyl ether yields 460 mg of 7α-acetylthio-1α,2α;15α,16α-dimethylene-3-oxo-17α-pregn-4-ene-21,17-carbolactone, mp 246° C. (under decomposition). UV: $\epsilon_{234} = 15,600$ (in methanol).

E

7α-Acetylthio-1α,2α;15β,16β-dimethylene-3-oxo-17α-pregn-4-ene-21,17-carbolactone 1. A solution of 5.0 g of 15β,16β-methylene-3-oxo-17α-pregna-4,6-diene-21,17-carbolactone in 100 ml of toluene is combined with 5.0 g of 2,3-dichloro-5,6-dicyano-1,4-benzoquinone and heated to 80° C. for 20 hours. The cooled reaction solution is filtered over silica gel, then washed with diethyl ether, and the yield is 4.54 g of a crude product which is once again chromatographed on silica gel. With 9–12% acetone-dichloromethane, 3.88 g of amorphous 15β,16β-methylene-3-oxo-17α-pregna-1,4,6-triene-21,17-carbolactone is eluted. $[\alpha]_D = +10°$ (in chloroform). UV: $\epsilon_{225} = 10,000$, $\epsilon_{255} = 8,200$, $\epsilon_{301} = 10,800$ (in methanol).

2. A solution of 6.09 g of trimethylsulfoxonium iodide in 58 ml of dimethyl sulfoxide is combined under argon with 1.1 g of a 55% suspension of sodium hydride in mineral oil and stirred for 2 hours at room temperature. Then 3.88 g of 15β,16β-methylene-3-oxo-17α-pregna-1,4,6-triene-21,17-carbolactone in solid form is added thereto. The reaction mixture is stirred for another hour and then poured into ice water. The thus-precipitated product is filtered off, washed with water, and dried, and chromatographed on silica gel. With 50–60% diethyl ether-dichloromethane, 3.49 g is eluted which, recrystallized from dichloromethanediisopropyl ether, yields 2.25 g of 1α,2α;15β,16β-dimethylene-3-oxo-17α-pregna-4,6-diene-21,17-carbolactone, mp 232.4° C. $[\alpha]_D = +198°$ (in chloroform). UV: $\epsilon_{282} = 20,600$ (in methanol).

3. At 60° C., 2 ml of thioacetic acid is added dropwise to a solution of 4.7 g of 1α,2α;15β,16β-dimethylene-3-oxo-17α-pregna-4,6-diene-21,17-carbolactone in 15 ml of methanol, and the mixture is stirred for 5 hours at this temperature. After cooling, the mixture is diluted with chloroform, washed with sodium bicarbonate and water, dried over magnesium sulfate, and concentrated under vacuum. The resultant crude product is purified by column chromatography on silica gel, thus obtaining 2.84 g of 7α-acetylthio-1α,2α;15β,16β-dimethylene-3-oxo-17α-pregn-4-ene-21,17-carbolactone, mp 257°–259° C. UV: $\epsilon_{235} = 16,600$ (in methanol).

F.

7α-Carboxy-15α,16α-methylene-3-oxo-17α-pregn-4-ene-21,17-carbolactone

1. A solution of 3.6 g of 15α,16α-methylene-3-oxo-17α-pregna-4,6-diene-21,17-carbolactone in 50 ml of absolute tetrahydrofuran is combined dropwise with 25 ml of a 1.8-molar diethylaluminum cyanide solution in toluene, and the mixture is stirred for 4 hours at room temperature. In order to work up the mixture, it is combined with 50 ml of methanol, agitated for one hour at 5° C. and for one hour at room temperature, the precipitated aluminum salt is suctioned off over silica gel, washed with methanol, and concentrated under vacuum. The resultant residue is taken up in 30 ml of methanol and stirred with 1 g of potassium carbonate for 1.5 hours. After the potassium carbonate has been suctioned off, the mixture is concentrated under vacuum. The thus-obtained crude product is purified by column chromatography, yielding 2.21 g of 7α-cyano-15α,16α-methylene-3-oxo-17α-pregn-4-ene-21,17-carbolactone, mp 260.2° C. $[\alpha]_D = +45°$ (in chloroform). UV: $\epsilon_{234} = 16,000$ (in methanol).

2. 21.3 ml of a 20% strength solution of diisobutyl aluminum hydride in toluene is added dropwise to a solution, cooled to −40° C., of 1.94 g of 7α-cyano-15α,16α-methylene-3-oxo-17α-pregn-4-ene-21,17-carbolactone in 100 ml of absolute dichloromethane, and the mixture is stirred for 90 minutes. In order to work up the mixture, it is stirred into potassium-sodium tartrate solution, agitated for 30 minutes, extracted with ethyl acetate, and washed neutral with water. After drying over magnesium sulfate, the mixture is concentrated under vacuum, thus obtaining 1.59 g of 3β,5'-dihydroxy-15 α, 16α-methylene-4-androstene[(17β-1')-spiro-2']perhydrofuran-7α-carbaldehyde.

3. At −10° C., 4.7 ml of Jones solution is added dropwise to a solution of 1.5 g of 3β,5'-dihydroxy-15α,16α-methylene-4-androstene[(178β-1')spiro-2']perhydrofuran-7α-carbaldehyde in 60 ml of acetone, and the mixture is stirred for 30 minutes at this temperature. In order to work up the mixture, it is combined with 0.5 ml of methanol, diluted with ethyl acetate, the organic phase is extracted with dilute sodium hydroxide solution, the aqueous phase is washed with ethyl acetate, acidified with sulfuric acid, extracted with ethyl acetate, and washed with semiconcentrated sodium chloride solution until the mixture is neutral. After drying over magnesium sulfate, the mixture is concentrated under vacuum, thus obtaining 696 mg of 7α-carboxy-15α,16α-methylene-3-oxo-17α-pregn-4-ene-21,17-carbolactone.

UV: $\epsilon_{242} = 14,500$ (in methanol).

G.

7α-Carboxy-α,2α-methylene-3-oxo-17α-pregn-4-ene-21,17-carbolactone

1. A solution of 15.7 g of trimethylsulfoxonium iodide in 150 ml of dimethyl sulfoxide is combined under argon with 2.84 g of a 55% suspension of sodium hydride in mineral oil and stirred until a clear solution is obtained. Thereafter 10 g of 3-oxo-17α-pregna-1,4,6-triene-21,17-carbolactone is added in solid form. The mixture is worked up after 45 minutes by pouring into ice water weakly acidified with hydrochloric acid. The precipitated product is filtered off, washed with water, dried, and then chromatographed on silica gel. Recrystallization from acetone-hexane yields 8.73 g of 1α,2α-methylene-3-oxo-17α-pregna-4,6-diene-21,17-carbolactone, mp 253.7° C. $[\alpha]_D = +176°$ (in chloroform).

UV: $\epsilon_{282} = 21,100$ (in methanol).

2. A solution of 1.0 g of 1α,2α-methylene-3-oxo-17α-pregna-4,6-diene-21,17-carbolactone in 20 ml of dimethylformamide is combined with 600 mg of potassium cyanide, 350 mg of ammonium chloride, and 2 ml of water and heated for 2.5 hours to 100° C. The reaction mixture is stirred into ice water, the precipitated product is filtered off, washed with water, and dried. The crude product is chromatographed on silica gel. With 12–15% dichloromethane-acetone, 980 mg is eluted which, when recrystallized from dichloromethanediisopropyl ether, yields 587 mg of 7α-cyano-1α,2α-methylene-3-oxo-17α-pregna-4,6-diene-21,17-carbolactone, mp 244.3° C. $[\alpha]_D = +210°$ (in chloroform). UV: $\epsilon_{231} = 14,000$ (in methanol).

3. A solution is prepared from 3.40 g of 7α-cyano-1α,2-methylene-3-oxo-17α-pregna-4,6-diene-21,17-carbolactone and 200 ml of absolute toluene. The solution is cooled to −50° C., combined under argon dropwise with 35 ml of a 20% solution of diisobutyl aluminum hydride and stirred for one hour at −40° C. Then the excess reagent is decomposed by adding 5 ml of amyl alcohol, and the reaction mixture is stirred into ice-cooled potassium-sodium tartrate solution. The mixture is extracted with ethyl acetate, the organic phase is dried with sodium sulfate, and the solvent is evaporated under vacuum, yielding 3.41 g of 3β,5'-dihydroxy-1α,2α-methylene-4-androstene[(17β-1')spiro-2']perhydrofuran-7α-carbaldehyde as a crude product.

4. A solution of 3.41 g of 3β,5'-dihydroxy-1α,2α-methylene-4-androstene[(17β-1')spiro-2']perhydrofuran-7α-carbaldehyde in 75 ml of concentrated acetic acid is combined with 10.4 ml of Jones reagent. After 15 minutes, the mixture is combined with 1 ml of ethanol and stirred into ice water saturated with sodium chloride. The organic phase is extracted with sodium sulfate and the solvent evaporated under vacuum. As the residue, 3.18 g of 7α-carboxy-1α,2α-methylene-3-oxo-17α-pregn-4-ene-21,17-carbolactone is obtained.

H.
7α-Carboxy-1α,2α;15β,16β-dimethylene-3-oxo-17α-pregn-4-ene-21,17-carbolactone 1. A solution of 5.0 g of 15β,16β-methylene-3-oxo-17α-pregna-4,6-diene-21,17-carbolactone in 100 ml of toluene is combined with 5.0 g of 2,3-dichloro-5,6-dicyano-1,4-benzoquinone and heated for 20 hours to 80° C. The cooled reaction solution is filtered over silica gel, washed with diethyl ether, and the yield is 4.54 g of a crude product which is once more chromatographed on silica gel. With 9–12% acetone-dichloromethane 3.88 g of amorphous 15β,16β-methylene-3-oxo-17β-pregna-1,4,6-triene-21,17-carbolactone is eluted. $[\alpha]_D = +10°$ (in chloroform). UV: $\epsilon_{255} = 8,200$, $\epsilon_{301} = 10,800$ (in methanol).

2. A solution of 6.09 g of trimethylsulfoxonium iodide in 58 ml of dimethyl sulfoxide is combined under argon with 1.1 g of a 55% suspension of sodium hydride in mineral oil and stirred for 2 hours at room temperature. Then 3.88 g of 15β,16β-methylene-3-oxo-17α-pregna-1,4,6-triene-21,17-carbolactone is added in solid form. The reaction mixture is stirred for another hour and then poured into ice water. The precipitated product is filtered off, washed with water, and dried, and chromatographed on silica gel. With 50–60% diethyl ether-dichloromethane, 3.49 g is eluted which, when recrystallized from dichloromethane-diisopropyl ether, yields 2.25 g of 1α,2α;15β,16β-dimethylene-3-oxo-17α-pregna-4,6-diene-21,17-carbolactone, mp 232.4° C. $[\alpha]_D = +198°$ (in chloroform). UV: $\epsilon_{282} = 20,600$ (in methanol).

3. 4.0 g of 1α,2α;15β,16β-dimethylene-3-oxo-17α-pregna-4,6-diene-21,17-carbolactone is dissolved in 80 ml of dimethylformamide and combined with 8 ml of water, 4.0 g of potassium cyanide, and 2.0 g of ammonium chloride. The reaction mixture is maintained for 7 hours at a temperature of 80° C. and then subjected to water precipitation. The thus-precipitated product is isolated and chromatographed on silica gel. With 8–10% acetone-dichloromethane, 3.96 g of 7α-cyano-1α,2α;15β,16β-dimethylene-3-oxo-17α-pregn-4-ene-21,17-carbolactone is obtained. A sample, recrystallized from dichloromethane-diethyl ether, melts at 288.2° C. $[\alpha]_D = +206°$ (in chloroform). UV: $\epsilon_{232} = 13,700$ (in methanol).

4. A solution of 3.7 g of 7α-cyano-1α,2α;15β,16β-dimethylene-3-oxo-17α-pregn-4-ene-21,17-carbolactone in 315 ml of absolute toluene is combined at −40° C. under argon with 37 ml of a 20% solution of diisobutyl aluminum hydride and stirred at this temperature for one hour. The reaction mixture is added under agitation to 200 ml of a sodium-potassium tartrate solution. Then the mixture is extracted with ethyl acetate; the extract is dried with sodium sulfate and evaporated under vacuum. The residue consists of 3.67 g of 3β,5'-dihydroxy-1α,2α;15β,16β-dimethylene-4-androstene-[(17β-1')spiro-2']perhydrofuran-7α-carbaldehyde.

5. A solution is prepared from 3.67 g of 3β,5'-dihydroxy-1α;2α;15β,16β-dimethylene-4-androstene[(17β-1')spiro2']perhydrofuran-7α-carbaldehyde and 150 ml of acetone, and the solution is combined with 11.5 ml of Jones reagent. After adding 1 ml of ethanol, the mixture is poured into ice water and extracted with dichloromethane. The organic phase is washed with sodium bicarbonate solution and water, dried, and concentrated under vacuum, thus obtaining 3.56 g of 7α-carboxy-1α,-2α;15β,16β-dimethylene-3-oxo-17α-pregn-4-ene-21,17-carbolactone.

I.
7α-Carboxy-1α,2α;15α,16α-dimethylene-3-oxo-17α-pregn-4-ene-21,17-carbolactone 1. 5.0 g of 15α,16α-methylene-3-oxo-17α-pregna-4,6-diene-21,17-carbolactone is stirred in 50 ml of dioxane with 5.0 g of 2,3-dichloro-5,6-dicyano-1,4-benzoquinone for 3 hours at 100° C. The reaction solution is then cooled, the precipitated hydroquinone is suctioned off and washed with dioxane. The filtrate is exhaustively concentrated under vacuum. The residue is taken up in diethyl ether, washed with sodium bicarbonate solution and water, dried, and evaporated. Chromatography on silica gel yields 3.46 g of 15α,16α-methylene-3-oxo-17α-pregna-1,4,6-triene-21,17-carbolactone. UV: $\epsilon_{222} = 11,250$, $\epsilon_{254} = 9,140$, $\epsilon_{299} = 11,500$ (in methanol).

2. 8.8 g of trimethylsulfoxonium iodide is stirred in 99 ml of dimethyl sulfoxide with 1.39 g of sodium hydride, a 55% oil suspension, until the hydride is dissolved. Then, under argon, 2.8 g of 15α,16α-methylene-3-oxo-17α-pregna-1,4,6-triene-21,17-carbolactone is added, and the mixture is stirred for 2 hours at room temperature. The reaction solution is stirred into ice water, weakly acidified with 2N sulfuric acid, and the thus-formed precipitate is filtered off. After dissolving in methylene chloride, the mixture is washed with water, dried, and evaporated. The residue is chromatographed on silica gel, thus obtaining 2.1 g of 1α,2α;15α, 16α-dimethylene-3-oxo-17α-pregna-4,6-diene-21,17-carbolactone. UV: $\epsilon_{281} = 19,500$ (in methanol).

3. Under argon, 1.5 g of 1α,2α;15α,16α-dimethylene-3-oxo-17α-pregna-4,6-diene-21,17-carbolactone is stirred in 50 ml of absolute tetrahydrofuran with 8.2 ml of a 1.8-molar diethylaluminum cyanide solution in toluene for 17 hours at room temperature. The reaction solution is then introduced into a potassium-sodium tartrate solution. The crude product obtained by extraction with diethyl ether is stirred in 38 ml of methanol with 45 mg of potassium carbonate for 2 hours at room temperature. The solution is diluted with ether, washed with water, and dried. The residue is chromatographed on silica gel. After trituration with diisopropyl ether, 600 mg of 7α-cyano-1α,2α,15α,16α-dimethylene-3-oxo-17α-pregn-4-ene-21,17-carbolactone is obtained, mp >300° C.

4. 620 mg of 7α-cyano-1α,2α;15α,16α-dimethylene-3-oxo-17α-pregn-4-ene-21,17-carbolactone is stirred in 115 ml of toluene with 6.2 ml of a 20% diisobutyl aluminum hydride solution in toluene for 30 minutes at −40° C. under argon. After adding 100 ml of potassium-sodium tartrate solution, the mixture is extracted with ethyl acetate. The organic phase is dried with sodium sulfate and evaporated under vacuum. The residue consists of 650 mg of 3β,5′-dihydroxy-1α,2α;15α,16α-dimethylene-4-androstene[(17β-1′)-spiro-2′]perhydrofuran-7α-carbaldehyde.

5. A solution of 530 mg of 3β,5′-dihydroxy-1α,2α;1-5α,16α-dimethylene-4-androstene[(17β-1′)spiro-2′]perhydrofuran-7α-carbaldehyde in 10.6 ml of acetone is stirred for 30 minutes at 0° C. with 1 ml of Jones reagent (prepared from 267 g of chromium(VI) oxide, 230 ml of concentrated sulfuric acid, filled up to 1000 ml with water). The mixture is combined with dichloromethane, washed with water, dried over sodium sulfate, and concentrated under vacuum. The residue consists of 520 mg of 7α-carboxy-1α,2α;15α,16α-dimethylene-3-oxo-17α-pregn-4-ene-21,17-carbolactone.

J.
3,5′-Bis(tert-butyldimethylsilyloxy)-1α,2α-methylene-4-androstene[(17β-1′)spiro-2′perhydrofuran-7α-carbaldehyde 1. A solution of 15.7 g of trimethylsulfoxonium iodide in 150 ml of dimethyl sulfoxide is combined under argon with 2.84 g of a 55% suspension of sodium hydride in mineral oil and stirred until a clear solution is obtained Then 10 g of 3-oxo-17α-pregna-1,4,6-triene-21,17-carbolactone is added in solid form. The mixture is worked up after about 45 minutes by pouring into ice water weakly acidified with hydrochloric acid. The thus-precipitated product is filtered off, washed with water, dried, and then chromatographed on silica gel. Recrystallization from acetone-hexane yields 8.73 g of 1α,2α-methylene-3-oxo-17α-pregna-4,6-diene-21,17-carbolactone, mp 253.7° C. $[\alpha]_D = +176°$ (in chloroform). UV: $\epsilon_{282} = 21,100$ (in methanol).

2. A solution of 1.0 g of 1α,2α-methylene-3-oxo-17α-pregna-4,6-diene-21,17-carbolactone in 20 ml of dimethylformamide is combined with 600 mg of potassium cyanide, 350 mg of ammonium chloride, and 2 ml of water, and heated for 2.5 hours to 100° C. The reaction mixture is stirred into ice water, the precipitated product is filtered off, washed with water, and dried. The crude product is chromatographed on silica gel. Elution with 12–15% dichloromethaneacetone yields 980 mg of product which, recrystallized from dichloromathane-diisopropyl ether, produces 587 mg of 7α-cyano-1α,2α-methylene-3-oxo-17α-pregna-4,6-diene-21,17-carbolactone, mp 244.3° C. $[\alpha]_D = +210°$ (in chloroform). UV: $\epsilon_{231} = 14,000$ (in methanol).

3. 3.4 g of 7α-cyano-1α,2α-methylene-3-oxo-17α-pregna-4,6-diene-21,17-carbolactone is dissolved in 200 ml of absolute toluene. The solution is cooled to −50° C., combined dropwise under argon with 39 ml of a 20% solution of diisobutyl aluminum hydride, and stirred for one hour at −40° C. Thereafter the excess reagent is decomposed by adding 5 ml of amyl alcohol, and the reaction mixture is stirred into ice-cooled potassium-sodium tartrate solution. The mixture is extracted with ethyl acetate, the organic phase is dried with sodium sulfate, and the solvent is evaporated under vacuum, thus obtaining 3.41 g of 3β,5′-dihydroxy-1α,2α-methylene-4-androstene[(17β-1′)spiro-2′]perhydrofuran-7αcarbaldehyde as a crude product.

4. A solution is prepared from 1.1 g of 3β,5′-dihydroxy-1α,2α-methylene-4-androstene[(17β-1′)spiro-2′]perhydrofuran-7α-carbaldehyde and 12 ml of dimethylformamide. The solution is combined under ice cooling with 0.6 g of imidazole and 1.9 g of tert-butyldimethylsilyl chloride in 4 ml of dimethylformamide and thereafter stirred for 3 hours at room temperature. The mixture is poured into ice water, the precipitate is filtered off and taken up in diethyl ether. The solution is washed with water, dried with sodium sulfate, and evaporated under vacuum. The residue is chromatographed on silica gel. With 6–10% diethyl ether-pentane, 860 mg of 3,5′-bis(tert-butyldimethylsilyloxy)-1α,-2α-methylene-4-androstene[(17β-1′)spiro-2′]perhydrofuran-7α-carbaldehyde is eluted.

K.
3,5′-Bis(tert-butyldimethylsilyloxy)-1α,-2α;15β,16β-dimethylene-4-androstene[(17β-1′)spiro-2′]perhydrofuran-7α-carbaldehyde 1. A solution of 5.0 g of 15β,16β-methylene-3-oxo-17α-pregna-4,6-diene-21,17-carbolactone in 100 ml of toluene is combined with 5.0 g of 2,3-dichloro-5,6-dicyano-1, 4-benzoquinone and heated for 20 hours to 80° C. The cooled reaction solution is filtered over silica gel, washed with diethyl ether, and 4.54 g of a crude product is thus obtained which is once more chromatographed on silica gel. Elution with 9–12% acetone-dichloromethane yields 3.88 g of amorphous 15β,16β-methylene-3-oxo-17α-pregna-1,4,6-triene-21,17-carbolactone. $[\alpha]_D = +10°$ (in chloroform). UV: $\epsilon_{225} = 10,000$, $\epsilon_{225} = 8,200$, $\epsilon_{301} = 10,800$ (in methanol).

2. A solution of 6.09 g of trimethylsulfoxonium iodide in 58 ml of dimethyl sulfoxide is combined under argon with 1.1 g of a 55% suspension of sodium hydride in mineral oil and stirred for 2 hours at room temperature. Then 3.88 g of 15β,16β-methylene-3-oxo-17α-pregna-1,4,6-triene-21,17-carbolactone is added in solid form. The reaction mixture is stirred for another hour and then poured into ice water. The thus-precipitated product is filtered off, washed with water, and dried, and chromatographed on silica gel. Elution with 50–60% diethyl ether-dichloromethane yields 3.49 g which, when recrystallized from dichloromethane-diisopropyl ether, produces 2.25 g of 1α,2α;15β, 16β-dimethylene-3-oxo-17α-pregna-4,6-diene-21,17-carbolactone, mp 232.4° C. $[\alpha]_D = +198°$ (in chloroform). UV: $\epsilon_{282} = 20,600$ (in methanol).

3. 4.0 g of 1α,2α;15β,16β-dimethylene-3-oxo-17α-pregna-4,6-diene-21,17-carbolactone is dissolved in 80 ml of dimethylformamide and combined with 8 ml of water, 4.0 g of potassium cyanide, and 2.0 g of ammonium chloride. The reaction mixture is maintained for 7 hours at a temperature of 80° C. and then subjected to water precipitation. The thus-precipitated product is isolated and chromatographed on silica gel. With 8–10% acetone-dichloromethane, 3.96 g of 7α-cyano-1α,2α;15β,16β-dimethylene-3-oxo-17α-pregn-4-ene-21,17-carbolactone is obtained. A sample, recrystallized from dichloromethane-diethyl ether, melts at 288.2° C. $[\alpha]_D = +206°$ (in chloroform). UV: $\epsilon_{232} = 13,700$ (in methanol).

4. A solution of 3.7 g of 7α-cyano-1α,2α;15β,16β-dimethylene-3-oxo-17α-pregn-4-ene-21,17-carbolactone in 315 ml of absolute toluene is combined at −40° C. under argon with 37 ml of a 20% solution of diisobutyl aluminum hydride and stirred at this temperature for one hour. The reaction mixture is added under agitation to 200 ml of a sodium-potassium tartrate solution. Subsequently the mixture is extracted with ethyl acetate, the extract is dried with sodium sulfate, and evaporated under vacuum. The residue consists of 3.67 g of 3β,5′- dihydroxy-1α,2α;15β,16β-dimethylene-4-androstene-[(17β-1')spiro-2']perhydrofuran-7α-carbaldehyde.

5. A solution of 2.26 g of 3β,5'-dihydroxy-1α,-2α;15β,16β-dimethylene-4-androstene[(17β-1')spiro-2']perhydrofuran-7α-carbaldehyde in 23 ml of dimethylformamide is combined under ice cooling with 3.3 g of tert-butyldimethylsilyl chloride in 8 ml of dimethylformamide and stirred for 2 hours at room temperature. After ice water precipitation, the product is filtered off and taken up in diethyl ether. The solution is washed with water, dried, and evaporated under vacuum. The crude product is 3.04 g of 3,5'-bis(tert-butyldimethylsilyloxy)-1α,2α;15β,16β-dimethylene-4-androstene-[(17β-1')spiro-2']perhydrofuran-7α-carbaldehyde.

L.

3,5'-Bis(tert-butyldimethylsilyloxy)-1α,2α;15α,16α-dimethylene-4-androstene[(17β-1')spiro-2']perhydrofuran-7α-carbaldehyde 1. 5.0 g of 15α,16α-methylene-3-oxo-17α-pregna-4,6-diene-21,17-carbolactone is stirred in 50 ml of dioxane with 5.0 g of 2,3-dichloro-5,6-dicyano-1,4-benzoquinone for 3 hours at 100° C. The reaction solution is then cooled, the precipitated hydroquinone is suctioned off and washed with dioxane. The filtrate is extensively concentrated under vacuum. The residue is taken up in diethyl ether, washed with sodium bicarbonate solution and water, dried, and evaporated. Chromatography on silica gel yields 3.46 g of 15α,16α-methylene-3-oxo-17α-pregna-1,4,6-triene-21,17-carbolactone. UV: $\epsilon_{222}=11,250$, $\epsilon_{254}=9,140$, $\epsilon_{299}=11,500$ (in methanol).

2. 8.8 g of trimethylsulfoxonium iodide is stirred in 99 ml of dimethyl sulfoxide with 1.39 g of sodium hydride, a 55% oil suspension, until the hydride is dissolved. Then, under argon, 2.8 g of 15α,16α-methylene-3-oxo-17α-pregna-1,4,6-triene-21,17-carbolactone is added, and the mixture is further stirred for 2 hours at room temperature. The reaction solution is stirred into ice water, weakly acidified with 2N sulfuric acid, and the thus-formed precipitate is filtered off. After dissolving in methylene chloride, the mixture is washed with water, dried, and evaporated. The residue is chromatographed on silica gel, thus obtaining 2.1 g of 1α,2α;15α,16α-dimethylene-3-oxo-17α-pregna-4,6-diene-21,17-carbolactone. UV: $\epsilon_{281}=19,500$ (in methanol).

3. Under argon, 1.5 g of 1α,2α;15α,16α-dimethylene-3-oxo-17α-pregna-4,6-diene-21,17-carbolactone is stirred in 50 ml of absolute tetrahydrofuran with 8.2 ml of a 1.8-molar diethylaluminum cyanide solution in toluene for 17 hours at room temperature. The reaction solution is then introduced into a potassium-sodium tartrate solution. The crude product obtained by extraction with diethyl ether is stirred in 38 ml of methanol with 45 mg of potassium carbonate for 2 hours at room temperature. The solution is diluted with ether, washed with water, and dried. The residue is chromatographed on silica gel. After trituration with diisopropyl ether, 600 mg of 7α-cyano-1α,2α;15α,16α-dimethylene-3-oxo-17α-pregn-4-ene-21,17-carbolactone is obtained, mp >300° C.

4. Under argon, 620 mg of 7α-cyano-1α,2α;15α,16α-dimethylene-3-oxo-17α-pregn-4-ene-21,17-carbolactone is stirred in 115 ml of toluene with 6.2 ml of a 20% diisobutyl aluminum hydride solution in toluene for 30 minutes at −40° C. After adding 100 ml of potassium-sodium tartrate solution, the mixture is extracted with ethyl acetate. The organic phase is dried with sodium sulfate and evaporated under vacuum. The residue consists of 650 mg of 3β,5'-dihydroxy-1α,2α;15α,16α-dimethylene-4-androstene[(17β-1')spiro-2']perhydrofuran-7α-carbaldehyde.

5. A solution of 1.0 g of 3β,5'-dihydroxy-1α,2α;15α,16α-dimethylene-4-androstene[(17β-1')spiro-2']perhydrofuran-7α-carbaldehyde in 10 ml of dimethylformamide is combined with 0.5 g of imidazole and 1.8 g of tert-butyldimethylsilyl chloride in 4 ml of dimethylformamide and stirred for 3 hours at room temperature. The mixture is poured into ice water, the precipitate is filtered off and taken up in diethyl ether. The solution is washed with water, dried over sodium sulfate, and evaporated under vacuum. The residue is chromatographed, thus obtaining 750 mg of 3,5'-bis(tert-butyldimethylsilyloxy)-1α,2α;15α,16α-dimethylene-4-androstene[(17β-1')spiro-2']perhydrofuran-7α-carbaldehyde.

EXAMPLE 1

A solution of 1.0 g of 7α-acetylthio-1α,2α-methylene-3-oxo-17α-pregn-4-ene-21,17-carbolactone in 37 ml of methanol is combined under an argon atmosphere with 5.5 ml of a 1-molar potassium ethylate solution in methanol and agitated. After 10 minutes, the solution is combined with 1 ml of acetic acid and poured into ice water. The thus-precipitated product is extracted with ethyl acetate. The extract is washed with water, dried over sodium sulfate, and concentrated under vacuum. The residue is chromatographed on silica gel. Elution with 18–20% diethyl ether-dichloromethane yields 450 mg of a crystalline product which is recrystallized from dichloromethane-diisopropyl ether. Yield: 340 mg of 7α-mercapto-1α,2α-methylene-3-oxo-17α-pregn-4-ene-21,17-carbolactone, mp 239.7° C. $[\alpha]_D=+190°$ (in chloroform).

UV: $\epsilon_{232}=13,100$ (in methanol).

EXAMPLE 2

4.0 g of 1α,2α-methylene-3-oxo-17α-pregna-4,6-diene-21,17-carbolactone is dissolved in 40 ml of methanol and 4 ml of piperidine. Under ice cooling, methanethiol is introduced from a steel bottle into the solution over a period of 30 minutes. Subsequently the mixture is allowed to stand at room temperature for 15 hours and thereafter poured into ice water. The thus-precipitated product is filtered off, washed with water, dried, and chromatographed on silica gel. Elution with 8.8–10.3% acetone-dichloromethane produces 2.99 g which is recrystallized from hexane-dichloromethanediisopropyl ether. Yield: 1.80 g of 1α,2α-methylene-7α-methylthio-3-oxo-17α-pregn-4-ene-21,17-carbolactone, mp 174.0° C. $[\alpha]_D=+137°$ (in chloroform).

UV: $\epsilon_{236}=13,500$ (in methanol).

EXAMPLE 3

A solution of 3.0 g of 1α,2α-methylene-3-oxo-17α-pregna-4,6-diene-21,17-carbolactone in 30 ml of methanol and 3 ml of piperidine is combined with 3 ml of ethanethiol. The reaction mixture is stirred for 15 hours at room temperature and thereafter poured into ice water. The precipitated product is filtered off, washed with water, and taken up in dichloromethane. The solution is washed with water, dried with sodium sulfate, and concentrated under vacuum. The residue is chromatographed on silica gel. With ethyl acetatehexane (1:1), 3.31 g is eluted which, recrystallized from dichloromethane-diisopropyl ether, yields 2.45 g of 7α-ethylthio-1α,2α-methylene-3-oxo-17α-pregn-4-ene- 21,17-carbolactone, mp 205.5° C. $[\alpha]_D = +115°$ (in chloroform). UV: $\epsilon_{236} = 13,500$ (in methanol).

EXAMPLE 4

Under the conditions described in Example 3, 3.0 g of 1α,2α-methylene-3-oxo-17α-pregna-4,6-diene-21,17-carbolactone is reacted with 1-propanethiol. The reaction product is worked up and purified accordingly. Yield: 1.57 g of 1α,2α-methylene-3-oxo-7α-propylthio-17α-pregn-4-ene-21,17-carbolactone, mp 191.2° C. $[\alpha]_D = +103°$ (in chloroform). UV: $\epsilon_{236} = 13,800$ (in methanol).

EXAMPLE 5

Under the conditions disclosed in Example 3, 1.5 g of 1α,2α-methylene-3-oxo-17α-pregna-4,6-diene-21,17-carbolactone is converted, in the presence of 2-propanethiol, into 1α,2α-methylene-3-oxo-7α-(2-propylthio)-17α-pregn-4-ene-21,17-carbolactone. Yield: 891 mg, mp 239.4° C. (from dichloromethane-diisopropyl ether). $[\alpha]_D = +107°$ (in chloroform).
UV: $\epsilon_{237} = 14,000$ (in methanol).

EXAMPLE 6

Under the conditions given in Example 3, 1.0 g of 1α,2α-methylene-3-oxo-17α-pregna-4,6-diene-21,17-carbolactone is converted, in the presence of 1-butanethiol, into 7α-butylthio-1α,2α-methylene-3-oxo-17α-pregn-4-ene-21,17-carbolactone. Yield: 762 mg (from dichloromethanediisopropyl ether). $[\alpha]_D = +99°$ (in chloroform).
UV: $\epsilon_{235} = 13,900$ (in methanol).

EXAMPLE 7

Under the conditions indicated in Example 3, 2.0 g of 1α,2α-methylene-3-oxo-17α-pregna-4,6-diene-21,17-carbolactone is converted, in the presence of 2-mercaptoethanol, into 7α-(2-hydroxyethylthio)-1α,2α-methylene-3-oxo-17α-pregn-4-ene-21,17-carbolactone. Yield: 1.83 g (from dichloromethane-diisopropyl ether).
$[\alpha]_D = +106°$ (in chloroform).
UV: $\epsilon_{236} = 13,650$ (in methanol).

EXAMPLE 8

A solution of 6.75 g of 7α-acetylthio-3-oxo-17α-pregna-1,4-diene-21,17-carbolactone in 250 ml of methanol is combined with 36.8 ml of a 1-molar potassium ethylate solution in methanol and stirred for 10 minutes under an argon atmosphere. After adding 4 ml of concentrated acetic acid, the mixture is stirred into ice water and extracted with diethyl ether. The organic phase is washed with water, dried, and concentrated under vacuum. The residue is chromatographed on silica gel. Elution with 18–33% ethyl acetate-diethyl ether produces 5.09 g which, recrystallized from acetone-diisopropyl ether, yields 3.87 g of 7α-mercapto-3-oxo-17α-pregna-1,4-diene-21,17-carbolactone, mp 210.8° C. $[\alpha]_D = +19°$ (in chloroform). UV: $\epsilon_{240} = 19,900$ (in methanol).

EXAMPLE 9

A solution of 2.0 g of 7α-methylthio-3-oxo-17α-pregn-4-ene-21,17-carbolactone in 40 ml of toluene is heated, after adding 2.0 g of 2,3-dichloro-5,6-dicyano-1,4-benzoquinone, for 20 hours to 80° C. Then the mixture is cooled and filtered. The filtrate is concentrated under vacuum and the residue chromatographed on silica gel. Elution with ethyl acetate yields 880 mg of product which is recrystallized from dichloromethane-diisopropyl ether, thus producing 435 mg of 7α-methylthio-3-oxo-17α-pregna-1,4-diene-21,17-carbolactone, mp 229.4° C. $[\alpha]_D = -56°$ (in chloroform). UV: $\epsilon_{242} = 15,400$ (in methanol).

EXAMPLE 10

A suspension, cooled to 0° C., of 642 mg of 7α-acetylthio-15β,16β-methylene-3-oxo-17α-pregn-4-ene-21,17-carbolactone in 5 ml of methanol and 8 ml of tetrahydrofuran is combined dropwise with 277 mg of potassium ethylate in 7 ml of methanol, and the mixture is stirred for one hour. The mixture is worked up by diluting with dichloromethane, washed with dilute sulfuric acid and water, dried over magnesium sulfate, and concentrated under vacuum. The resultant crude product is purified by column chromatography, thus obtaining 344 mg of 7α-mercapto-15β,16β-methylene-3-oxo-17α-pregn-4-ene-21,17-carbolactone, mp 246.4° C. $[\alpha]_D = +58°$ (in chloroform). UV: $\epsilon_{236} = 14,400$ (in methanol).

EXAMPLE 11

Under the conditions described in Example 10, starting with 640 mg of 7α-acetylthio-15β,16β-methylene-3-oxo-17α-pregna-1,4-diene-21,17-carbolactone, 296 mg of 7α-mercapto-15β,16β-methylene-3-oxo-17α-pregna-1,4-diene-21,17-carbolactone is obtained, mp 258.7° C. $[\alpha]_D = +17°$ (in chloroform).

EXAMPLE 12

Under the conditions disclosed in Example 10, using 730 mg of 7α-acetylthio-1α,2α;15β,16β-dimethylene-3-oxo-17α-pregn-4-ene-21,17-carbolactone as the starting compound, 460 mg of 7α-mercapto-1α,2α;15β,16β-dimethylene-3-oxo-17α-pregn-4-ene-21,17-carbolactone is produced, mp 259.6° C. $[\alpha]_D = +180°$ (in chloroform).

EXAMPLE 13

Under the conditions indicated in Example 2, 1.2 g of 15β,16β-methylene-3-oxo-17α-pregna-4,6-diene-21,17-carbolactone is converted into 15β,16β-methylene-7α-methylthio-3-oxo-17α-pregn-4-ene-21,17-carbolactone. Yield: 1.08 g, mp 268.7° C. (from diisopropyl ether).
UV: $\epsilon_{238} = 16,000$ (in methanol).

EXAMPLE 14

Under the conditions described in Example 3, 500 mg of 15β,16β-methylene-3-oxo-17α-pregna-4,6-diene-21,17-carbolactone is converted into 7α-ethylthio-15β,16β-methylene-3-oxo-17α-pregn-4-ene-21,17-carbolactone. Yield: 450 mg, mp 261.2° C. (from diisopropyl ether).
UV: $\epsilon_{238} = 16,400$ (in methanol).

EXAMPLE 15

Under the conditions of Example 3, 500 mg of 15β,16β-methylene-3-oxo-17α-pregna-4,6-diene-21,17-carbolactone is converted with 1-propanethiol into 15β,16β-methylene-3-oxo-7α-propylthio-17α-pregn-4-ene-21,17-carbolactone. Yield: 360 mg mp 259.6° C. (from acetone). UV: $\epsilon_{241} = 15,300$ (in methanol).

EXAMPLE 16

Under the conditions described in Example 3, 500 mg of 15β,16β-methylene-3-oxo-17α-pregna-4,6-diene-21,17-carbolactone is converted in the presence of 1- butanethiol into 7α-butylthio-15β,16β-methylene-3-oxo-17α-pregn-4-ene-21,17-carbolactone. Yield 390 mg, mp 262.7° C. (from acetone).

UV: $\epsilon_{241} = 15,600$ (in methanol).

EXAMPLE 17

A solution of 600 mg of 15β,16β-methylene-7α-methylthio-3-oxo-17α-pregn-4-ene-21,17-carbolactone in 12 ml of dioxane is combined with 660 mg of 2,3-dichloro-5,6-dicyano-1,4-benzoquinone and stirred for 17 hours at 100° C. The reaction mixture is diluted with diethyl ether, washed with sodium bicarbonate solution and water, dried, and evaporated. The residue is chromatographed on silica gel. After trituration with diisopropyl ether, 145 mg of 15β,16β-methylene-7α-methylthio-3-oxo-17α-pregna-1,4-diene-21,17-carbolactone is obtained, mp 265.3° C.

UV: $\epsilon_{244} = 15,400$ (in methanol).

EXAMPLE 18

Under the conditions described in Example 3, 500 mg of 15β,16β-methylene-3-oxo-17α-pregna-4,6-diene-21,17-carbolactone is converted in the presence of 2-mercaptoethanol into 7α-(2-hydroxyethylthio)-15β,16β-methylene-3-oxo-17α-pregn-4-ene-21,17-carbolactone. Yield: 530 mg, mp 233.2° C. (from diisopropyl ether). UV: $\epsilon_{238} = 15,400$ (in methanol).

EXAMPLE 19

A solution of 920 mg of 7α-(2-hydroxyethylthio)-15β,16β-methylene-3-oxo-17α-pregn-4-ene-21,17-carbolactone in 18.5 ml of dioxane is combined with 920 mg of 2,3-dichloro-5,6-dicyano-1,4-benzoquinone and stirred for 16 hours at 80° C. The reaction mixture is worked up and the reaction product isolated analogously to Example 17. Yield: 185 mg of 7α-(2-hydroxyethylthio)-15β,16β-methylene-3-oxo-17α-pregna-1,4-diene-21,17-carbolactone, mp 250° C. (from diisopropyl ether). UV: $\epsilon_{243} = 14,900$ (in methanol).

EXAMPLE 20

400 mg of 7α-(2-hydroxyethylthio)-15β,16β-methylene-3-oxo-17α-pregn-4-ene-21,17-carbolactone is dissolved in a mixture of 1.6 ml of pyridine and 0.8 ml of acetic anhydride. The solution is allowed to stand for 2.5 hours at room temperature and then poured into ice water. The thus-precipitated product is suctioned off, washed with water, dried, and chromatographed on silica gel. After recrystallization from acetone-diisopropyl ether, 275 mg of 7α-(2-acetoxyethylthio)-15β,16β-methylene-3-oxo-17α-pregn-4-ene-21,17-carbolactone is obtained, mp 195.9° C. UV: $\epsilon_{238} = 16,150$ (in methanol).

EXAMPLE 21

Under the conditions set forth in Example 3, 500 mg of 15β,16β-methylene-3-oxo-17α-pregna-4,6-diene-21,17-carbolactone is converted by reaction with 1-mercaptopropan-2-ol into 7α-(2-hydroxypropylthio)-15β,16β-methylene-3-oxo-17α-pregn-4-ene-21,17-carbolactone. Yield: 419 mg, mp 250.3° C. (from acetone-diisopropyl ether). UV: $\epsilon_{238} = 16,200$ (in methanol).

EXAMPLE 22

444 mg of 7α-acetylthio-15α,16α-methylene-3-oxo-17α-pregn-4-ene-21,17-carbolactone is saponified under the conditions of Example 8. After chromatography and recrystallization from diisopropyl ether, 220 mg of 7α-mercapto-15α,16α-methylene-3-oxo-17α-pregn-4-ene-21,17-carbolactone is obtained, mp 215.3° C. UV: $\epsilon_{234} = 14,100$ (in methanol).

EXAMPLE 23

Under the conditions described in Example 3, 500 mg of 15α,16α-methylene-3-oxo-17α-pregna-4,6-diene-21,17-carbolactone is reacted with 2-mercaptoethanol. Yield: 365 mg of 7α-(2-hydroxyethylthio)-15α,16α-methylene-3-oxo-17α-pregn-4-ene-21,17-carbolactone, mp 213.8° C.

UV: $\epsilon_{240} = 16,650$ (in methanol).

EXAMPLE 24

Under the conditions of Example 3, 500 mg of 1α,2α;15β,16β-dimethylene-3-oxo-17α-pregna-4,6-diene-21,17-carbolactone is reacted with 2-mercaptoethanol. Yield: 385 mg of 7α-(2-hydroxyethylthio)-1α,2α;15β,16β-dimethylene-3-oxo-17α-pregn-4-ene-21,17-carbolactone, mp 235.2° C. (from diisopropyl ether-acetone).

UV: $\epsilon_{240} = 12,700$ (in methanol).

EXAMPLE 25

Under the conditions set forth in Example 3, 500 mg of 1α,2α;15β,16β-dimethylene-3-oxo-17α-pregna-4,6-diene-21,17-carbolactone is reacted with 1-mercaptopropan-2-ol. Reaction period: 3 days. Yield: 345 mg of 7α-(2-hydroxypropylthio)-1α,2α;15β,16β-dimethylene-3-oxo-17α-pregn-4-ene-21,17-carbolactone, mp 242° C. (from acetone-diisopropyl ether). UV: $\epsilon_{236} = 13,900$ (in methanol).

EXAMPLE 26

780 mg of 7α-acetylthio-1α,2α;15α,16α-dimethylene-3-oxo-17α-pregn-4-ene-21,17-carbolactone is saponified under the conditions of Example 8, thus obtaining 250 mg of 7α-mercapto1α,2α;15α,16α-dimethylene-3-oxo-17α-pregn-4-ene-21, 17-carbolactone, mp 234.1° C. (from acetone-diisopropyl ether). UV: $\epsilon_{232} = 12,750$ (in methanol).

EXAMPLE 27

750 mg of 1α,2α;15α,16α-dimethylene-3-oxo-17α-pregna-4,6-diene-21,17-carbolactone is made to react with methanethiol as described in Example 2. Yield: 540 mg of 7α-methylthio-1α,2α;15α,16α-dimethylene-3-oxo-17α-pregn-4-ene-21, 17-carbolactone as a viscous oil. UV: $\epsilon_{237} = 12,900$ (in methanol).

EXAMPLE 28

Under the conditions of Example 2, 400 mg of 15α,16α-methylene-3-oxo-17α-pregna-4,6-diene-21,17-carbolactone yields 190 mg of 7α-methylthio-15α,16α-methylene-3-oxo-17α-pregn-4-ene-21,17-carbolactone, mp 197.6° C. (from diisopropyl ether). UV: $\epsilon_{238} = 14,800$ (in methanol).

EXAMPLE 29

500 mg of 1α,2α;15α,16α-dimethylene-3-oxo-17α-pregna-4,6-diene-21,17-carbolactone is reacted under the conditions of Example 3 with 2-mercaptoethanol. Yield: 440 mg of 7α-(2-hydroxyethylthio)-1α,2α;15α,16α-dimethylene-3-oxo-17α-pregn-4-ene-21,17-carbolactone as an oil. UV: $\epsilon_{234} = 11,800$ (in methanol).

EXAMPLE 30

1.2 g of 1α,2α;15β,16β-dimethylene-3-oxo-17α-pregna-4,6-diene-21,17-carbolactone is converted under the conditions of Example 2 into 1α,2α;15β,16β-dimethylene-7α-methylthio-3-oxo-17α-pregn-4-ene-21,17-carbolactone. Yield: 875 mg, mp 121.7° C. (from diethyl ether-diisopropyl ether). $[\alpha]_D = +118°$ (in chloroform). UV: $\epsilon_{237} = 13,000$ (in methanol).

EXAMPLE 31

1.2 g of 1α,2α;15β,16β-dimethylene-3-oxo-17α-pregna-4,6-diene-21,17-carbolactone is converted under the conditions of Example 3 into 7α-ethylthio-1α,2α;15β,16β-dimethylene-3-oxo-17α-pregn-4-ene-21,17-carbolactone. Yield: 1.06 g (from dichloromethane-diisopropyl ether). $[\alpha]_D = +109°$ (in chloroform). UV: $\epsilon_{236} = 13,700$ (in methanol).

EXAMPLE 32

Under the conditions of Example 3, 500 mg of 1α,2α;15β,16β-dimethylene-3-oxo-17α-pregna-4,6-diene-21,17-carbolactone is reacted with 3-mercaptopropan-1-ol, thus obtaining 275 mg of 7α-(3-hydroxypropylthio)-1α,2α;15β,16β-dimethylene-3-oxo-17α-pregn-4-ene-21,17-carbolactone, mp 241.7° C. UV: $\epsilon_{236} = 14,100$ (in methanol).

EXAMPLE 33

7α-Methylthio-15α,16α-methylene-3-oxo-17α-pregna-1,4-diene-21,17-carbolactone

Under the conditions described in Example 9, starting with 420 mg of 7α-methylthio-15α,16α-methylene-3-oxo-17α-pregn-4-ene-21,17-carbolactone, 195 mg of 7α-methylthio-15α,16α-methylene-3-oxo-17α-pregna-1,4-diene-21,17-carbolactone is produced.

UV: $\epsilon_{242} = 14,500$ (methanol).

EXAMPLE 34

A diazomethane solution is added dropwise to a solution of 690 mg of 7α-carboxy-15α,16α-methylene-3-oxo-17α-pregn-4-ene-21,17-carbolactone in 10 ml of tetrahydrofuran until the yellow coloring is persistent. The excess diazomethane is decomposed with acetic acid and the mixture concentrated under vacuum. The resultant crude product is purified by column chromatography and recrystallized from methanol, thus obtaining 631 mg of 7α-methoxycarbonyl-15α,16α-methylene-3-oxo-17α-pregn-4-ene-21,17-carbolactone, mp 187.4° C. $[\alpha]_D = +9.1°$ (in chloroform). UV: $\epsilon_{240} = 15,200$ (in methanol).

EXAMPLE 35

A solution of 1.2 g of 7α-carboxy-1α,2α-methylene-3-oxo-17α-pregn-4-ene-21,17-carbolactone in 40 ml of tetrahydrofuran is combined with 20 ml of an ethereal diazomethane solution prepared from 750 mg of N-nitrosomethylurea. After 30 minutes, the mixture is combined with 1 ml of acetic acid and concentrated under vacuum. The residue is chromatographed on silica gel. With 30–47% diethyl ether-dichloromethane, 810 mg is eluted which is recrystallized from dichloromethane-diisopropyl ether. Yield: 521 mg of 7α-methoxycarbonyl-1α,2α-methylene-3-oxo-17α-pregn-4-ene-21,17-carbolactone, mp 268°–274° C. $[\alpha]_D = +156°$ (in chloroform). UV: $\epsilon_{238} = 12,300$ (in methanol).

EXAMPLE 36

A solution of 1.2 g of 7α-carboxy-1α,2α-methylene-3-oxo-17α-pregn-4-ene-21,17-carbolactone in 5 ml of dichloromethane is combined with 40 mg of 4-dimethylaminopyridine, 600 mg of dicyclohexylcarbodiimide, as well as with 1 ml of ethanol. After 15 minutes, the mixture is suctioned off from the thus-produced N,N'-dicyclohexylurea, and the filtrate is evaporated under vacuum. The residue is repeatedly chromatographed on silica gel. With 20–22% acetone-hexane, 460 mg is finally eluted which, when recrystallized from dichloromethane-diisopropyl ether, yields 322 mg of 7α-ethoxycarbonyl-1α,2α-methylene-3-oxo-17α-pregn-4-ene-21,17-carbolactone, mp 244.8° C. $[\alpha]_D = +138°$ (in chloroform). UV: $\epsilon_{240} = 13,400$ (in methanol).

EXAMPLE 37

Under the conditions indicated in Example 3 but using 2-propanol in place of ethanol, 1.0 g of 7α-carboxy-1α,2α-methylene-3-oxo-17α-pregn-4-ene-21,17-carbolactone yields 293 mg of 7α-isopropoxycarbonyl-1α,2α-methylene-3-oxo-17α-pregn-4-ene-21,17-carbolactone, mp 240°–242° C. $[\alpha]_D = +124°$ (in chloroform). UV: $\epsilon_{240} = 13,700$ (in methanol).

EXAMPLE 38

Under the conditions set forth in Example 2, 1.30 g of 7α-carboxy-1α,2α;15β,16β-dimethylene-3-oxo-17α-pregn-4-ene-21,17-carbolactone is reacted with diazomethane. The crude product is chromatographed on silica gel. Elution with 82–91% ethyl acetate-hexane yields 960 mg which, when recrystallized from dichloromethane-diisopropyl ether, produces 777 mg of 7α-methoxycarbonyl-1α,2α;15β,16β-dimethylene-3-oxo-17α-pregn-4-ene-21,17-carbolactone, mp 260.9° C. $[\alpha]_D + 150°$ (in chloroform). UV: $\epsilon_{238} = 14,000$ (in methanol).

EXAMPLE 39

A solution of 500 mg of 7α-carboxy-1α,2α;15β,16β-dimethylene-3-oxo-17α-pregn-4-ene-21,17-carbolactone in 10 ml of dimethylformamide is combined with 1.0 g of silver oxide and 2 ml of bromoethane and stirred for 4.5 hours. The reaction mixture is filtered and the product is precipitated in the filtrate with ice water. After extraction with dichloromethane, the organic phase is washed with water, dried with sodium sulfate, and evaporated to dryness under vacuum. The residue is chromatographed on silica gel. With 10–12% acetone-dichloromethane, 364 mg is obtained which is recrystallized from dichloromethanediisopropyl ether. Yield: 274 mg of 7α-ethoxycarbonyl-1α,2α;15β,16β-dimethylene-3-oxo-17α-pregn-4-ene-21,17-carbolactone, mp 233.3° C. $[\alpha]_D = +146°$ (in chloroform). UV: $\epsilon_{238} = 13,600$ (in methanol).

EXAMPLE 40

Under the conditions described in Example 6, 700 mg of 7α-carboxy-1α,2α;15β,16β-dimethylene-3-oxo-17α-pregn-4-ene-21,17-carbolactone is allowed to react with 1-iodopropane. The reaction mixture is worked up after 30 minutes and chromatographed on silica gel. Elution with 31–32% acetone-hexane yields 520 mg which, when recrystallized from dichloromethane-diisopropyl ether, produces 357 mg of 7α-propoxycarbonyl-1α,2α;15β,16β-dimethylene-3-oxo-17α-pregn-4-ene-21,17-carbolactone, mp 180.9° C.

EXAMPLE 41

Under the conditions given in Example 6, 700 mg of 7α-carboxy-1α,2α;15β,16β-dimethylene-3-oxo-17α-pregn-4-ene-21,17-carbolactone is reacted with 2.9 ml of 2-iodopropane. After 30 minutes, the reaction mixture is worked up and chromatographed. With 30–32% acetone-hexane, 510 mg is eluted which, recrystallized from dichloromethane-diisopropyl ether, produces 428 mg of 7α-isopropoxycarbonyl-1α,2α;15β,16β-dimethylene-3-oxo-17α-pregn-4-ene-21,17-carbolactone, mp 214.0° C. $[\alpha]_D = +129°$ (in chloroform). Uv:$\epsilon_{239} = 13,500$ (in methanol).

EXAMPLE 42

Under the conditions described in Example 2, 520 mg of 7α-carboxy-1α,2α;15α,16α-dimethylene-3-oxo-17α-pregn-4-ene-21,17-carbolactone is made to react with diazomethane. The crude product is chromatographed and recrystallized from diisopropyl ether. Yield: 272 mg of 7α-methoxycarbonyl-1α,2α;15α,16α-dimethylene-3-oxo-17α-pregn-4-ene-21 17-carbolactone, mp 237.3° C. UV:$\epsilon_{238} = 13,400$ (in methanol).

EXAMPLE 43

A solution of 500 mg of 7α-methoxycarbonyl-15α,16α-methylene-3-oxo-17α-pregn-4-ene-21,17-carbolactone in 10 ml of dioxane is combined with 500 mg of 2,3-dichloro-5,6-dicyano-1,4-benzoquinone and heated to boiling for 16 hours. After cooling, the reaction mixture is filtered and concentrated under vacuum. The crude product is chromatographed on silica gel with dichloromethane-acetone, thus obtaining 220 mg of 7α-methoxycarbonyl-15α,16α-methylene-3-oxo-17α-pregna-1,4-diene-21,17-carbolactone. UV:$\epsilon_{241} = 16,700$ (in methanol).

EXAMPLE 44

205 mg of 7α-methoxycarbonyl-15α,16α-methylene-3-oxo-17α-pregn-4-ene-21,17-carbolactone is suspended in 2 ml of methanol and stirred with 28 mg of potassium hydroxide in 0.5 ml of water for 16 hours at room temperature and for one hour at 60° C., and concentrated under vacuum. The thus-obtained oil is dissolved in a small amount of ethanol and precipitated with diethyl ether, thus obtaining 120 mg of 17β-hydroxy-7α-methoxycarbonyl-15α,16α-methylene-3-oxo-17α-pregn-4-ene-21-carboxylic acid potassium salt.

EXAMPLE 45

A. 4.5 ml of a 1.4-molar solution of methyllithium in diethyl ether is added dropwise to a solution of 720 mg of 3,5'-bis(tert-butyldimethylsilyloxy)-15β,16β-methylene4-androstene[(17β-1')spiro-2']perhydrofuran-7α-carbaldehyde in 10 ml of absolute tetrahydrofuran, and the mixture is stirred for 2 hours at room temperature. To work up the mixture, it is combined with saturated ammonium chloride solution, extracted with ether, and washed neutral with water. After drying over magnesium sulfate, the mixture is concentrated under vacuum, thus obtaining 750 mg of 3 5'-bis(tert-butyldimethylsilyloxy)-7α-(1-hydroxyethyl)-15β,16β-methylene-4-androstene[(17β-1')spiro-2']perhydrofuran which is further reacted without purification.

B. At 0° C., 2.5 ml of Jones solution is added dropwise to a solution of 750 mg of 3,5'-bis(tert-butyldimethylsilyloxy)-7α-(1-hydroxyethyl)-15β,16β-methylene-4-androstene[(17β-1')spiro-2']perhydrofuran in 30 ml of acetone, and the mixture is stirred for one hour. For working up purposes, the mixture is combined with 0.5 ml of methanol, diluted with 200 ml of ethyl acetate, and washed neutral with water. After drying over magnesium sulfate, the mixture is concentrated under vacuum, and the resultant crude product is purified by column chromatography, thus obtaining 269 mg of 7α-acetyl-15β,16β-methylene-3-oxo-17α-pregn-4-ene-21,17-carbolactone, mp 255.7° C.

$[\alpha]_D = +76°$ (in chloroform). UV:$\epsilon_{241} = 14,175$ (in methanol).

EXAMPLE 46

A. 620 mg of 3,5'-bis(tert-butyldimethylsilyloxy)-15β,16β-methylene-4-androstene[(17β-1')spiro-2']perhydrofuran-7α-carbaldehyde in 5 ml of tetrahydrofuran is added dropwise to a Grignard solution prepared from 365 mg of magnesium and 1.15 ml of ethyl bromide in 30 ml of tetrahydrofuran; the mixture is heated under reflux for 2 hours. For working up purposes, the mixture is combined with saturated ammonium chloride solution, diluted with diethyl ether, and washed neutral with water. After drying over magnesium sulfate, the mixture is concentrated under vacuum. Yield: 635 mg of 3,5'-bis(tert-butyldimethylsilyloxy)-7α-(1-hydroxypropyl)-15β,16β-methylene-4-androstene[(17β-1')-spiro-2']perhydrofuran which is further reacted without purification.

B. Under the conditions described in Example 45-B, starting with 620 mg of 3,5'-bis(tert-butyldimethylsilyloxy)-7α-(1-hydroxypropyl)-15β,16β-methylene-4-androstene[(17β-1')-spiro-2']perhydrofuran, 270 mg of 15β,16β-methylene-3-oxo-7α-(1-oxopropyl)-17α-pregn-4-ene-21,17-carbolactone is obtained, mp 266.9° C. $[\alpha]_D = +65°$ (in chloroform).

UV:$\epsilon_{242} = 14,700$ (in methanol).

EXAMPLE 47

A. Under the conditions described in Example 45-A, 720 mg of 3,5'-bis(tert-butyldimethylsilyloxy)-15β,16β-methylene-4-androstene[(17β-1')spiro-2']perhydrofuran-7α-carbaldehyde and propylmagnesium bromide produce 786 mg of 3,5'-bis(tert-butyldimethylsilyloxy)-7α-(1-hydroxbutyl)-15β,16β-methylene-4-androstene[(17β-1')spiro-2']perhydrofuran.

B. Under the conditions disclosed in Example 45-B, starting with 780 mg of 3,5'-bis(tert-butyldimethylsilyloxy)-7α-(1-hydroxybutyl)-15β,16β-methylene-4-androstene[(17β-1')-spiro-2']perhydrofuran, 309 mg of 15β,16β-methylene-3-oxo-7α-(1-oxobutyl)-17α-pregn-4-ene-21,17-carbolactone is obtained, mp 258.7° C. $[\alpha]_D = +54°$ (in chloroform).

UV:$\epsilon_{241} = 14,500$ (in methanol).

EXAMPLE 48

A. Under the conditions indicated in Example 45-A, 730 mg of 3,5'-bis(tert-butyldimethylsilyloxy)-1α,2α-methylene-4-androstene[(17β-1')spiro-2']perhydrofuran-7α-carbaldehyde yields 850 mg of 3,5'-bis(tert-butyldimethylsilyloxy)-7α-(1-hydroxyethyl)-1α,2α-methylene-4-androstene-[(17β-1')spiro-2']perhydrofuran.

B. Under the conditions set forth in Example 45-B, starting with 840 mg of 3,5'-bis(tert-butyldimethylsilyloxy)-7α-(1-hydroxyethyl)-1α,2α-methylene-4-androstene[(17β-1')-spiro-2']perhydrofuran, 210 mg of 7α-acetyl-1α,2α-methylene-3-oxo-17α-pregn-4-ene-21,17-carbolactone is obtained, mp 183.7° C. (from dichloromethane-diisopropyl ether-hexane). [α]$_D$= +167° (in chloroform).
UV:ε$_{241}$=13,000 (in methanol).

EXAMPLE 49

A. Under the conditions described in Example 45-A, 1.5 g of 3,5'-bis(tert-butyldimethylsilyloxy)-1α,-2α;15β,16β-dimethylene-4-androstene[(17β-1')spiro-2']perhydrofuran-7α-carbaldehyde is converted into 3,5'-bis(tert-butyldimethylsilyloxy)-7α-(1-hydroxyethyl)-1α,2α;15β,16β-dimethylene-4-androstene[(17β-1')spiro-2']perhydrofuran. Yield: 1.57 g.

B. Under the conditions set forth in Example 45-B, starting with 1.57 g of 3,5'-bis(tert-butyldimethylsilyloxy)-7α-(1-hydroxyethy)-1α,2α;15β,16β-dimethylene-4-androstene-[(17β-1')spiro-2']perhydrofuran, 252 mg of 7α-acetyl-1α,2α;-15β,16β-dimethylene-3-oxo-17α-pregn-4-ene-21,17-carbolactone is produced, mp 195.5° C. (from dichloromethane-diisopropyl ether). [α]$_D$= +190° (in chloroform)
UV:ε$_{239}$=12,500 (in methanol).

EXAMPLE 50

A. Under the conditions disclosed in Example 45-A, 1.5 g of 3,5'-bis(tert-butyldimethylsilyloxy)-1α,-2α;15β,16βdimethylene-4-androstene[(17β-1')spiro-2']perhydrofuran-7α-carbaldehyde yields, by reacting with 6 ml of a 1.6-molar solution of butyllithium in hexane, 1.64 g of 3,5'-bis-(tert-butyldimethylsilyloxy)-7α-(1-hydroxypentyl)-1α,2α;15β,16β-dimethylene-4-androstene[(17β-1')spiro-2']perhydrofuran.

B. Under the conditions of Example 45-B, 1.64 g of 3,5'-bis(tert-butyldimethylsilyloxy)-7α-(1-hydroxypentyl)-1α,2α;15β,16β-dimethylene-4-androstene[(17β-1')spiro-2']perhydrofuran is converted into 249 mg of 1α,2α;15β,16β-dimethylene-3-oxo-7α-(1-oxopentyl)-17α-pregn-4-ene-21,17-carbolactone, mp 236.9° C. (from dichloromethanediisopropyl ether). [α]$_D$= +154° (in chloroform).
UV:ε$_{239}$=12,300 (in methanol).

EXAMPLE 51

A. Under the conditions disclosed in Example 45-A, 750 mg of 3,5'-bis(tert-butyldimethylsilyloxy)-1α,-2α;15β,16β-dimethylene-4-androstene[(17β-1')spiro-2']perhydrofuran-7α-carbaldehyde yields 630 mg of 3,5'-bis(tert-butyldimethylsilyloxy)-7α-(1-hydroxyethyl)-1α,2α;15α,16α-dimethylene-4-androstene[(17β-1')spiro-2']perhydrofuran.

B. Under the conditions of Example 45-B, 630 mg of 3,5'-bis(tert-butyldimethylsilyloxy)-7α-(1-hydroxyethyl)-1α,2α;15α,16α-dimethylene-4-androstrene-[(17β-1')spiro-2']perhydrofuran is converted into 249 mg of 7α-acetyl-1α,2α;15α,16α-dimethylene-3-oxo-17α-pregn-4-ene-21,17-carbolactone.
UV:ε$_{239}$=12,000 (in methanol).

EXAMPLE 52

205 mg of 7α-acetyl-15β,16β-methylene-3-oxo-17α-pregn-4-ene-21,17-carbolactone is suspended in 2 ml of methanol and stirred with 28 mg of potassium hydroxide in 0.5 ml of water for 16 hours at room temperature and one hour at 60° C., and concentrated under vacuum. The resultant oil is dissolved in a small amount of ethanol and precipitated with diethyl ether, thus obtaining 120 mg of 7α-acetyl-17β-hydroxy-15β,16β-methylene-3-oxo-17α-pregn-4-ene-21-carboxylic acid potassium salt.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 7α-substituted 3-oxo-17α-(pregn-4-ene-21,17-carbolactone of the formula

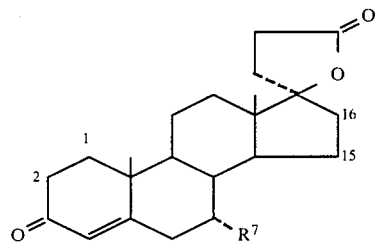

wherein

is a CC single bond, a CC double bond, or

R$^7$ is SR', wherein R' is hydrogen, C$_{1-6}$-alkyl or C$_{1-6}$-alkyl substituted by hydroxy or C$_{1-4}$-alkanoyloxy, or COR'', wherein R'' is C$_{1-4}$-alkyl; and

is a CC single bond,

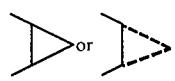

2. 7α-Mercapto-1α,2α-methylene-3-oxo-17α-pregn-4-ene-21,17-carbolactone, a compound of claim 1.

3. 7α-Ethylthio-1α,2α-methylene-3-oxo-17α-pregn-4-ene-21,17-carbolactone, a compound of claim 1.

4. 7α-Mercapto-1α,2α;15β,16β-dimethylene-3-oxo-17α-pregn-4-ene-21,17-carbolactone, a compound of claim 1.

5. 7α-Methylthio-15β,16β-methylene-3-oxo-17α-pregn-4-21,17-carbolactone, a compound of claim 1.

6. 7α-Methylthio-15β,16β-methylene-3-oxo-17α-pregn-1,4-diene-21,17-carbolactone, a compound of claim 1.

7. 7α-(2-Hydroxyethylthio)-15β,16β-methylene-3-oxo-17α-pregn-4-ene-21,17-carbolactone, a compound of claim 1.

8. 7α-(2-Hyroxypropylthio)-15β,16β-methylene-3-oxo-17α-pregn-4-ene-21,17-carbolactone, a compound of claim 1.

9. 7α-Methylthio-1α,2α;15β,16β-dimethylene-3-oxo-17α-pregn-4-ene-21,17-carbolactone, a compound of claim 1.

10. 7α-ethylthio-1α,2α;15β,16β-dimethylene-3-oxo-17α-pregn-4-ene-21,17-carbolactone, a compound of claim 1.

11. 7α-Methylthio-1α,2α;15β,16β-dimethylene-3-oxo-17α-pregn-4-ene-21,17-carbolactone, a compound of claim 1.

12. A 7α-substituted 3-oxo-17α-pregn-4-ene-21,17-carbolactone of the formula

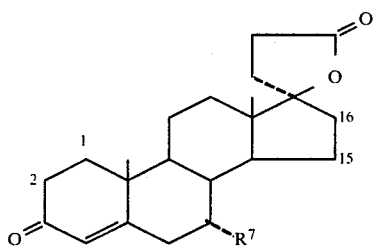

wherein

is

$R^7$ is COOR″, wherein R″ is $C_{1-4}$-alkyl; and

is a CC single bond,

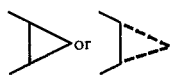

13. 7α-Ethoxycarbonyl-1α,2α-methylene-3-oxo-17α-pregn-4-ene-21,17-carbolactone, a compound of claim 12.

14. 7α-Methoxycarbonyl-1α,2α;15β,16β-dimethylene-3-oxo-17-α-pregn-4-ene-21,17-carbolactone, a compound of claim 12.

15. 7α-Ethoxycarbonyl-1α,2α;15β,16β-dimethyl-3-oxo-17α-pregn-4-ene-21,17-carbolactone, a compound of claim 12.

16. 7α-Isopropoxycarbonyl-1α,2α;15β,16β-dimethylene3-oxo-17α-pregn-4-ene-21,17-carbolactone, a compound of claim 12.

17. 7α-Methoxycarbonyl-1α,2α;15α,16α-dimethylene-3-oxo-17-pregn-4-ene-21,17-carbolactone, a compound of claim 12.

18. 7α-Acetyl-15β,16β-methylene-3-oxo-17α-pregn-4-ene-21,17-carbolactone, a compound of claim 1.

19. 7α-Acetyl-1α,2α;15β,16β-dimethylene-3-oxo-17α-pregn-4-ene-21,17-carbolactone, a compound of claim 1.

20. A compound of claim 1 wherein

is a CC double bond.

21. A compound of claim 1 wherein $R^7$ is SR′.

22. A compound of claim 21 wherein R′ is alkanoyloxy.

23. A compound of claim 21 wherein R′ is COR″.

24. A pharmaceutical composition containing an effective amount of a compound of claim 1 and a pharmacologically effective adjuvant.

25. A composition of claim 24, wherein said amount is 5–200 mg.

26. A method of treating an indication in a patient which is treatable by achieving an antialdosterone effect in the patient, comprising administering to the patient an amount of a compound of claim 1 effective to achieve an antialdosterone effect.

27. A method of claim 26 wherein the indication is edema.

28. A method of achieving a diuretic effect in a patient comprising administering to the patient a diuretically effective amount of a compound of claim 1.

29. A pharmaceutical composition containing an effective amount of a compound of claim 12 and a pharmacologically effective adjuvant.

30. A method of treating an indication in a patient which is treatable by achieving an antialdosterone effect in the patient, comprising administering to the patient an amount of a compound of claim 12 effective to achieve an antialdosterone effect.

31. A method of achieving a diuretic effect in a patient comprising administering to the patient a diuretically effective amount of a compound of claim 12.

32. A 7α-substituted 3-oxo-17α-pregn-4-ene-21, 17-carbolactone of the formula

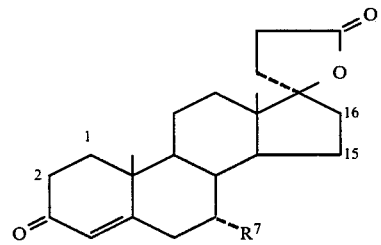

wherein

is a CC single bond, a CC double bond, or
$R^7$ is COOR″, wherein R″ is $C_{1-4}$alkyl; and
is a CC single bond.
* * * * *